US005505957A

United States Patent [19]
D'Angelo et al.

[11] Patent Number: 5,505,957
[45] Date of Patent: Apr. 9, 1996

[54] SELECTABLE DOSAGE TRANSDERMAL DELIVERY SYSTEM

[75] Inventors: Joseph P. D'Angelo; Henry Schur, both of Miami, Fla.

[73] Assignee: International Medical Associates, Inc., Miami, Fla.

[21] Appl. No.: 232,826

[22] Filed: Apr. 22, 1994

Related U.S. Application Data

[60] Division of Ser. No. 952,049, Sep. 28, 1992, Pat. No. 5,336,213, which is a continuation-in-part of Ser. No. 927,837, Aug. 10, 1992, which is a continuation-in-part of Ser. No. 865,309, Apr. 8, 1992, abandoned.

[51] Int. Cl.$^6$ ..................................................... A61R 13/00
[52] U.S. Cl. .......................... 424/449; 602/41; 602/43; 602/58; 604/304; 604/890.1
[58] Field of Search .................... 424/449; 604/890.1, 604/304; 602/41, 43, 58

[56] References Cited

U.S. PATENT DOCUMENTS

| | | | |
|---|---|---|---|
| 4,666,441 | 5/1987 | Andriola | 604/897 |
| 4,756,423 | 7/1988 | Holtsch | 206/533 |
| 4,904,475 | 2/1990 | Gale et al. | 424/449 |
| 4,917,676 | 4/1990 | Heiber et al. | 424/449 |
| 4,917,688 | 4/1990 | Nelson | 604/306 |
| 4,998,623 | 3/1991 | Doull | 206/531 |
| 5,064,422 | 11/1991 | Wick | 424/449 |
| 5,071,656 | 12/1991 | Lee et al. | 424/449 |

*Primary Examiner*—D. Gabrielle Phelan
*Attorney, Agent, or Firm*—Herbert L. Lerner; Laurence A. Greenberg

[57] ABSTRACT

A transdermal drug delivery system is disclosed. The system comprises a laminate composite of a patch/skin permeable membrane; a transfer gel layer disposed on said permeable membrane; a permeable membrane disposed on said transfer gel layer; a plurality of sectional drug reservoirs for receiving medicament disposed on the transfer gel layer; and activation means for releasing medicament from said drug reservoirs for contact with skin of a patient. The medicament in contained in the reservoirs at varying amounts and/or concentrations, providing for selectable dosage, for sequential delivery, for sequential activation, for variable unit dose drug delivery in transdermal application.

2 Claims, 11 Drawing Sheets

SELECTABLE DOSAGE TRANSDERMAL DELIVERY SYSTEM

CROSS-REFERENCE TO RELATED APPLICATIONS

This is a division of application Ser. No. 07/952,049 filed Sep. 28, 1992 now U.S. Pat. No. 5,336,213, which is a continuation-in-part of copending application Ser. No. 927,837, filed Aug. 10, 1992, which is a continuation-in-part of application Ser. No. 865,309, filed Apr. 8, 1992, now abandoned.

BACKGROUND OF THE INVENTION

1. Field of the Invention

The invention relates to transdermal delivery systems which allow for the variable dosage and or moltiple dosage of medicament in a patient controllable or pre-set format.

2. Description of the Related Art

Transdermal drug administration has recently come to the forefront as a useful route for continuous dosing of useful drugs where other means of administration are either discontinuous, labor intensive or where other routes present absorption or inactivation problems. Whereas per os administration has been time honored i.e. "a teaspoonful three times a day", such unit dose administration was subject to erratic blood levels of the actives due to non-uniform absorption from the gut due to other gut contents or inactivation of the drug actives by the digestion process or the normal action of the liver.

In addition, the need for active periodic administration i.e. three times a day, required active and willing participation by the patient or in home or hospital settings by the caregiver i.e. mother or nurse.

All these shortcomings are obviated by transdermal application where possible, of the drugs. A patch is adhered to a clear area of the skin and the drug is continually absorbed through the skin into the bloodstream for systemic distribution.

The skin is particularly useful as it presents large areas for drug administration, as the skin is the largest organ of the body. The utility of such a mode of administration has been demonstrated to those skilled in the art, as described, for example, in my copending application Ser. No. 865,309.

Almost any drug, at least to some degree, can be administrated transdermally. Reference is herewith had to U.S. Pat. Nos. 4,917,676, 3,598,122; 3,598,123; 3,742,951; 3,797,494; 3,948,254; 3,996,734; 4,284,444; and 4,597,961. Examples of such pharmacological actives include administration of antibacterial such as the penicillins, tetracyclines, second and third generation cephalosporins, chloramphenicol sulfonamides; sedatives and/or hypnotics, such as barbiturates, carbromal, antijussives such as codeine and dextromethorphan; anti-anxiety drugs such as the benzodiazepines including diazepam, buspirone; psychostimulants such as imipramine amitriptyline and other tricyclic antidepressants; anti psychotic drugs and tranquilizers such as lithium, chlorpromazine and haloperidol, reserpine, thiopropazate; Parkinsonism control agents such as bromotriptine, percolide, the anticholmergics including benzotropine, procyclidine, amantadine (also an antiviral); hormones and hormone antagonists and agonists, including adrenocorticosteroids; insulin, androgenic steroids, estrogenic and progestrogenic steroids, thyroxin and its agonist 5-FU(fluorouracil), tamoxifen; antipvretics and analgesics such as aspirin/acetaminophen and other non-steroidal anti-inflammatory drugs (NSAID), analgesics based on morphine; morphine antagonists; vasodilating agents such as nitroglycerine, isorbide dinitrate; alpha beta-blockers and other cardioactive drugs; antimalarials; anti-histamines and anticholinergics including atropine hyoscyamine or methscopalo-mine (for motion sickness; weaning agents such as nicotine for addiction to tobacco; and antiasthmatic bronchodilators such as formoterol; and combinations of such pharmaceutical actives.

Of course, while feasible, not all of these actives have yet been completely tested for efficacy by transdermal administration but many are under vigorous scrutiny. Other actives at this time are not economically viable for such administration, as the cost of full safety testing is too great for the specific number of patients involved.

As can be seen from this background discussion and the history of this type of medication, it is apparent that application by transdermal patch is a useful form for the administration of medication. However, a single dose per patch does not allow for clinical variations through adjustable dosage selection.

Various techniques of transdermal administration of drugs have been disclosed in the art. However, the prior art does not allow for variable dosage within a single patch or for sequential dosage within a single patch.

SUMMARY OF THE INVENTION

It is accordingly the main object of the invention to provide a selectable dosage, transdermal drug delivery system, which overcomes the hereinafore-mentioned disadvantages of the heretofore-known devices of this general type and which allows for sequential activation, variable dosage, sequential delivery and/or continuously selectable dosage in a single patch assembly.

It is a further object of this invention to deliver a clinical dosage of medicament over a range of clinically established dosages that may be predetermined by those skilled in the healing arts. For example: variable dosage selection.

It is another object of this invention that the dosage, once selected can be fixed in a "command-and-demand", non-alterable, patient-useable transdermal delivery system. For example: a physician can prescribe a particular dosage within the normal clinical range of the medicament and the pharmacist or other health care provider can preset that dosage on the patch so as to preempt potential error by the patient.

It is a further object of this invention that the delivery system is designed so that the integrity of the patch itself is not compromised by the setting of the dosage and remains in an aseptic condition until used by the patient. This is accomplished by providing the dosage setting device external to and removeable from the body of the patch. The present best mode embodiment of this invention is to have the patch contained within an outer package that will contain the herein described setting mechanism.

It is a further objective of this invention that the variable dosage patch may or may not be activated upon setting of the dosage. The activation may take place at a later time as required by the clinical condition. For example the pharmacist may set several patches, which remain set and the dosage unalterable because the setting mechanism has been removed. However the previously selected dosage of medicament is only released upon activation by the patient or attendant. This allows for the containment of medicament in a sealed environment thus preserving its biological activity until released to the transfer gel for delivery through the patch/skin interface membrane to the patient.

It is a further object of this invention that more than one medicament reservoir can be released for any given delivery. This provides the advantage of having the option for different medicament reservoirs to contain different medicaments, activators, enhancers or other chemicals which may be necessary or desirable for simultaneous delivery. Also, each medicament within each medicament reservoir will be isolated from the others during storage. Reference is herewith made to U.S. Pat. No. 4,666,441 owned by Ciba-Geigy Corp., which teaches the need for a plurality of reservoirs to separate incompatible medicaments.

It is another object of this invention to provide for a delivery system which, due to its multi-reservoir system with individually releasable options, allows for sequential delivery of a particular medicament over a prescribed time by activation by the patient.

It is a further object of this invention to provide each variable dosage or multiple dosage with a means to inform the wearer or attendant concerning the dosage, activation or set point for administration of each unit dose.

It is another object whereas a single application steady state dosing may not serve the best needs of the patient and be inconsistent with accepted clinical practice and to provide a method of multiple sequential dosing in those cases. Additionally, this invention allows for the variation where needed in dose levels within a single "patch".

Further objects and ancillary benefits will be apparent from the disclosure of the invention which consists of a variable dose and or multiple unit-dose transdermal patch assembly. This invention includes the various drugs that can be delivered in unit doses, configurations of such assemblies, storage of the drugs within the assembly and includes delivery systems for the drugs from storage areas in the assembly to the skin, various systems for activating each unit-dose of the assembly, various means for indicating activation of each unit-dose, and various means to assure that the dosages are only delivered upon command and demand by the patient and to prevent accidental release.

While the example above discloses a circular patch, the container form may also be rectangular, oval or irregular in form depending on positioning of the assembly on the body or limbs. Configuration of the assembly is dictated by the ultimate positioning of the assembly in areas where adhesion, absorption, and contact with clothes limbs and body hair are to be taken into account.

The number of unit doses included in each assembly depends on the size of the reservoirs to configure a convenient size. Generally four to ten unit doses are convenient with seven units preferred as permitting a single application of the drug once a day, or several times a day depending on the medicament and clinical application.

The principle of single unit doses in the multiple dose assembly is particularly useful as only a limited amount of the drug actives is exposed to the skin for transdermal absorption. When non-segregated multiple doses, as taught by the prior art are used, there arise problems.

With the foregoing and other objects in view there is provided, in accordance with the invention, a transdermal drug delivery system, comprising a laminate composite of:

(a) a patch/skin permeable membrane;

(b) a transfer gel layer disposed on the permeable membrane;

(c) a permeable membrane disposed on the transfer gel layer;

(d) a reservoir structure disposed above the permeable membrane, the reservoir structure having a plurality of drug reservoirs formed therein for receiving medicament;

(e) activation means for releasing medicament from the drug reservoirs for contact with skin of a patient.

In accordance with another feature of the invention, the drug delivery system includes a capillary distribution layer disposed between the permeable membrane and the reservoir structure, the capillary distribution layer being means for causing uniform distribution of medicament into the transfer gel and for assuring substantially complete emptying of a respectively activated drug reservoir.

In accordance with a further feature of the invention, the delivery system includes means for transferring the medicament from the drug reservoirs to the capilliary distribution space and for assuring complete and even draining of a respective drug reservoir upon activation. The transferring means may be effected by wicking action, by osmotic pressure or by a pressurized medicament well.

In accordance with an added feature of the invention, the reservoir structure with the drug reservoirs includes:

(a) an impervious lower layer having a plurality of windows formed therein, the windows including seal means to be punctured for releasing medicament from the reservoir for contact with the skin of the patient;

(b) an impervious upper layer disposed above the lower layer and having channels formed therein for receiving puncture pins and having a plurality of windows formed therein, the windows formed in the upper layer being aligned with the windows formed in the lower layer.

In accordance with again another feature of the invention, the activation means include a dial rotatably supported on the reservoir structure, puncture pins supported in the dial, and means for locking the dial in a respective rotational position after a given dosage of medicament is released.

In accordance with again an added feature of the invention, the delivery system includes means for preventing an accidental release of medicament.

In accordance with again a further feature of the invention, the delivery system includes indicator means for indicating initiation of administration of a unit dose from a respective reservoir upon activation. The indicator means may be of a visual, olfactory and auditory nature.

In accordance with again an additional feature of the invention, the delivery system includes means for securing the laminate composite to the skin of the patient.

In accordance with yet another feature of the invention, the reservoirs are provided to receive varying amounts and concentrations of medicament, and the delivery system includes means for selecting a given dosage of medicament to be administered by releasing medicament from a given reservoir.

In accordance with yet a further feature of the invention, the delivery system provides for individually and sequentially selecting given reservoirs for sequential administration of medicament to the skin of the patient.

With the objects of the invention in view, there is further provided, in accordance with yet an additional feature of the invention, a reservoir layer formed of micro-encapsulated medicament disposed above the permeable membrane. Variable amounts of medicament may be released by breaking only a given amount of microcapsules.

In accordance with a concomitant feature of the invention, the reservoir layer is formed of strips of micro-encapsulated medicament, the strips being separated from one another, and the activation means are in the form of a slide tab with a wedge mechanism for variably activating a given amount of microencapsulated medicament of a respective one of the strips.

Other features which are considered as characteristic for the invention are set forth in the appended claims.

Although the invention is illustrated and described herein as embodied in a selectable dosage, transdermal drug delivery system it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
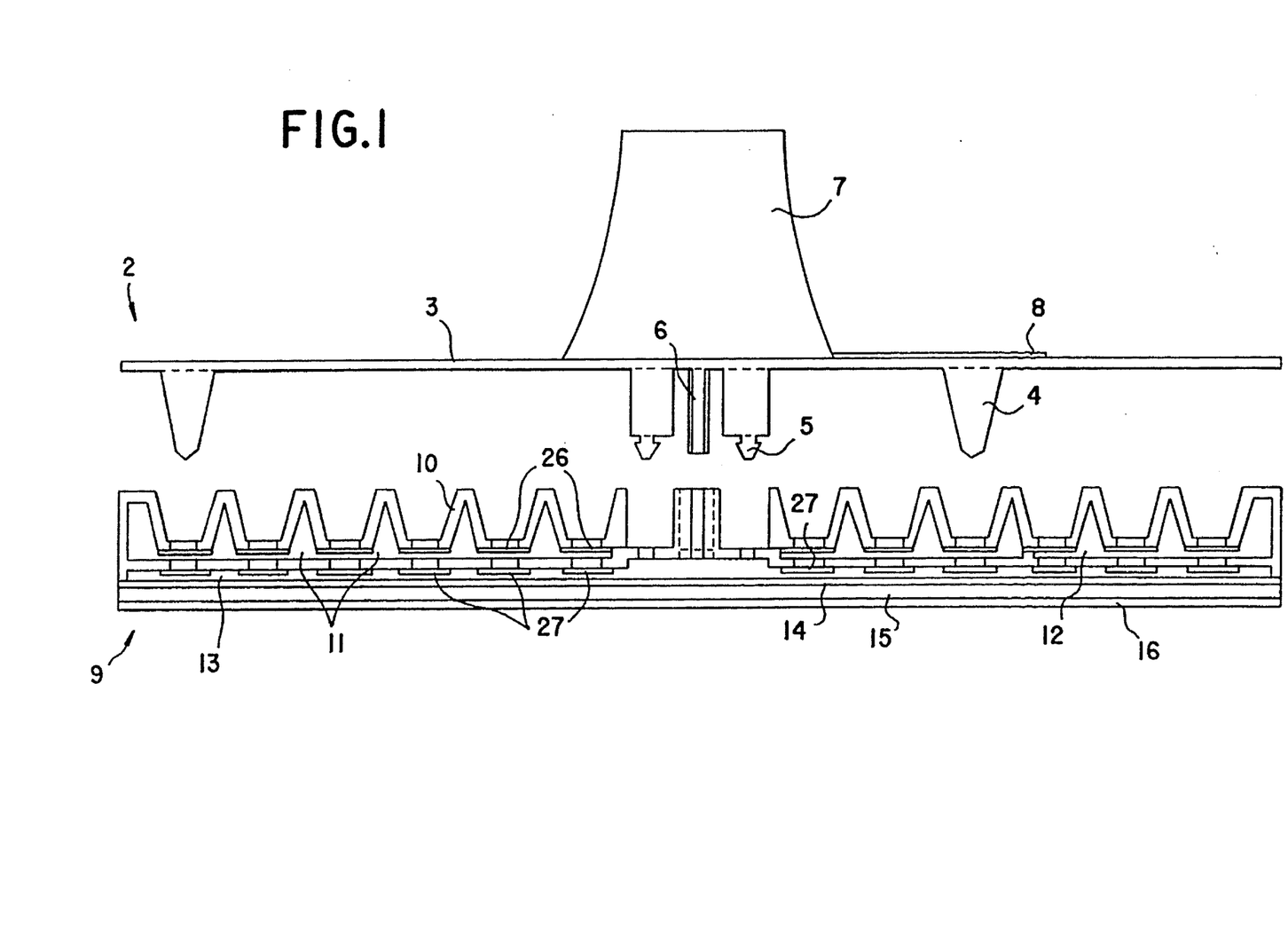
FIG. 1 is an elevational, cross-sectional, exploded view of a first embodiment of the delivery system hereinafter called the clock dial assembly.
Figure 2:
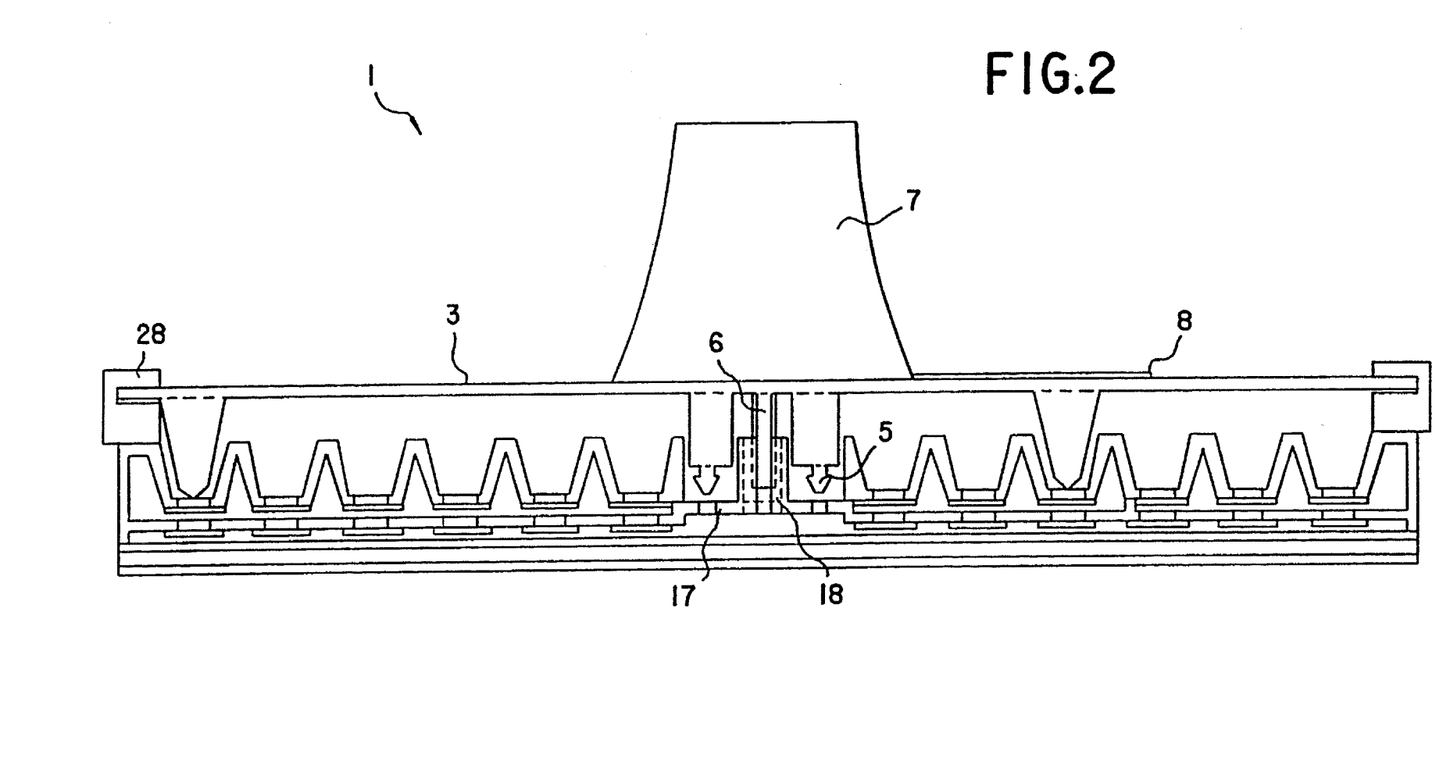
FIG. 2 is a cross-sectional view of the embodiment of FIG. 1 with the upper assembly and the lower assembly in a normal, abutting position prior to activation of the device.

Referring now to the figures of the drawing in detail and first, particularly, to FIGS. 1 and 2 thereof, there is seen an transdermal drug delivery system 1 which is comprised of an upper assembly 2 and lower assembly 9. The upper assembly 2 includes a molded solid disk or dial 3, and protruding therefrom a number of puncture pins 4, two locking pins 5, a fluted spindle 6, a pointer 8 and a dial knob 7.

The lower assembly 9 includes a grooved plate 10, through which the puncture pins 4 descend, thereby puncturing an upper film 26, and passing through a medicament 11 which is contained in sectional drug reservoirs 12, and then continuing to puncture through a lower film 27 and into a capillary distribution space 13. Medicament 11 flows past the puncture pins 4 into the capillary distribution space 13, thereby filling the space. The medicament 11 then diffuses through a protective membrane 14, into a transfer gel 15 and through a patch/skin interface membrane 16. At this point, the medicament is ready for absorption into the skin.

The position of the solid disk or dial 3 is controlled by turning the attached dial knob 7 to one of six positions which thereby sets the dosage. Prior to setting the dosage, a tamper-evident safety seal 28 must be removed. The solid disk 3 rotates clockwise with the fluted spindle 6 acting as an axis of rotation. The fluted spindle 6 and a cylinder 18 are each grooved in such a manner that only one position can be accessed at a time. After turning the dial 3 by means of the dial knob 7 to the desired position, and upon application of downward pressure, the upper assembly 2 descends, thus causing the locking pins 5 to engage in a locking ring 17 in the desired position. Once the locking pins 5 have engaged in the locking ring 17, the position of the dial 3 is permanently fixed and cannot be changed without the application of considerable force. As the upper assembly 2 descends and is locked into place, the puncture pins 4 rupture cellophane films 26 and 27, so that the respective sectional drug reservoir 12 releases the medicament 11 into the capillary distribution space 13 and into the transfer gel 15.

The dial know 7 may be attached to the solid disk 3 with adhesive. After the upper assembly 2 is locked into place, the dial 7 with the pointer 8 can be removed and discarded.

The ability to rotate solid disk 3 to set the dosage may also be accomplished by a separate key, which would obviate the necessity for the dial knob 7. Setting the dosage could then be accomplished by inserting the key into the like-keyed disk, rotating to the appropriate dosage and removing the key. This would provide the advantage of using one key to set a variety of clock dials.

Figure 3:
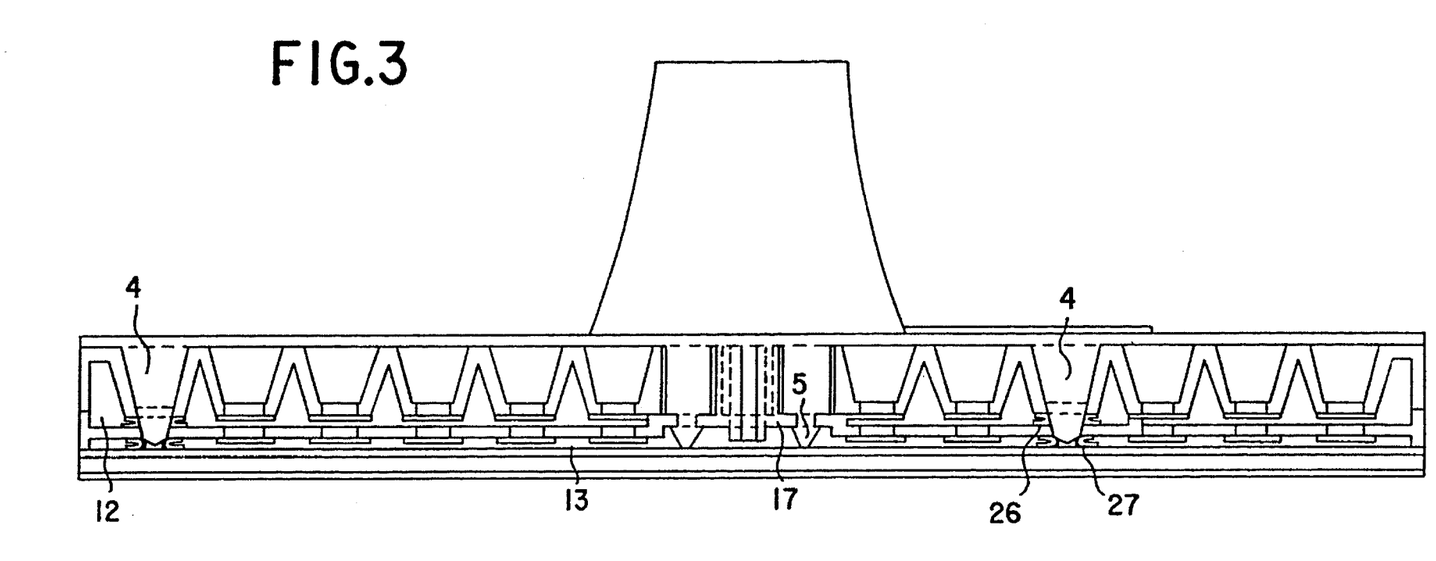
FIG. 3 is a cross-sectional view of the clock dial of FIG. 1 after the activation of the device.

Referring now to FIG. 3 in detail, there is shown the embodiment of FIGS. 1 and 2 in the activated state, but prior to the removal of the dial knob 7 and the pointer 8. The locking pins 5 have been engaged into the locking ring 17 and the puncture pins 4 have been lowered through the film seals 26 and 27 and the medicament flows from the sectional drug reservoirs 12 into the capillary distribution space 13.

Figure 4:
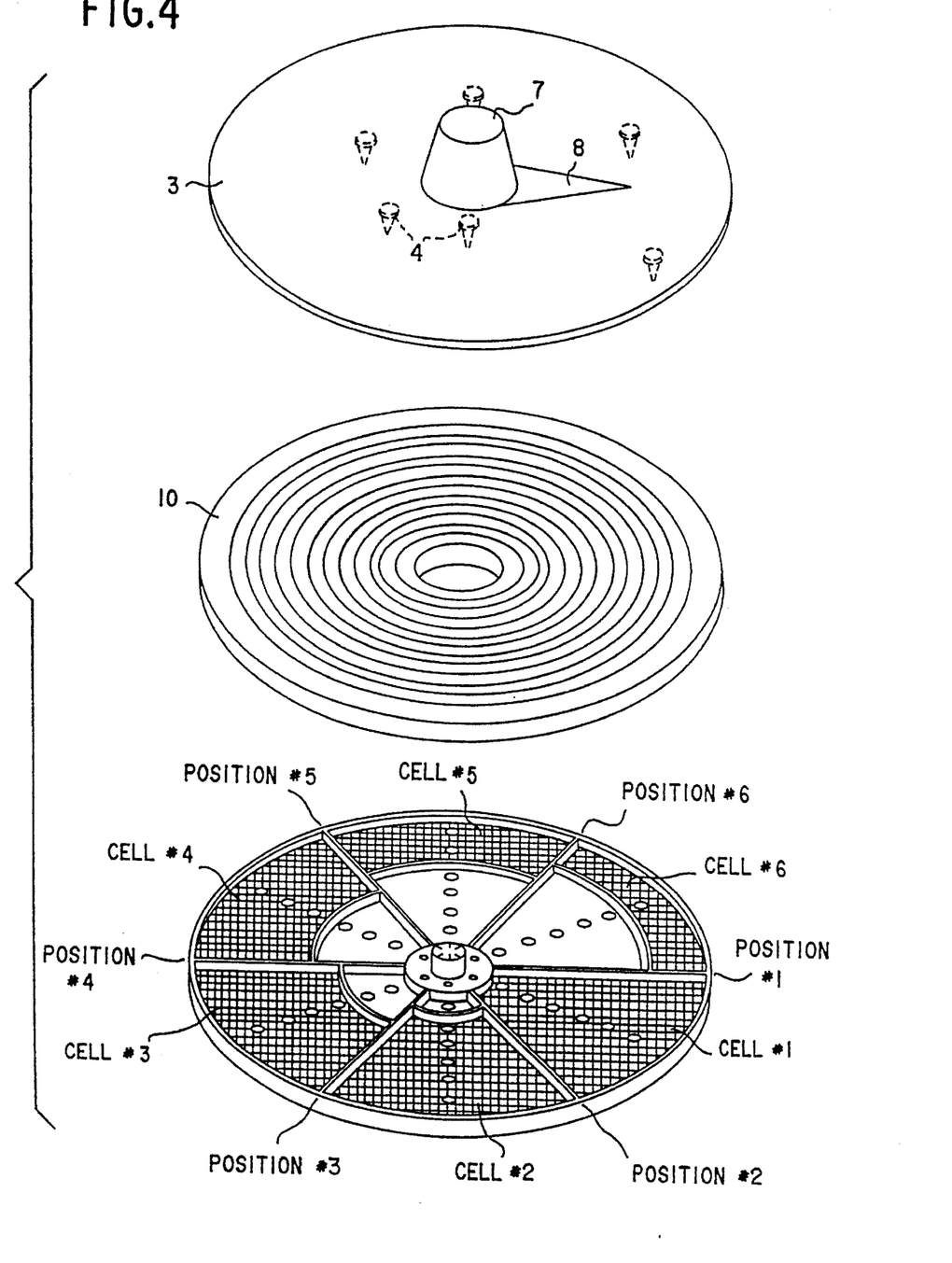
FIG. 4 is a perspective, exploded view of the clock dial embodiment with the dial or upper assembly, the grooved plate or middle assembly and the sectional drug reservoir or lower assembly shown separate from one another.

Referring now to the exploded views of FIG. 4 in detail, the upper assembly 2 is shown as the uppermost disk, and the lower assembly 9 has been separated into two disks, namely the grooved plate 10, in the middle, and the sectional drug reservoir 12, on the bottom. The puncture pins 4 ride in the grooved plate 10 and are rotated by dial 7 and pointer 8 until they are aligned with the appropriately selected drug reservoir, shown as cells 1–6.

In FIG. 4, the shaded area depicts that portion of the drug cell containing medicament 11 and the unshaded area depicts that portion of the drug cell without medicament. Located at the center of the circle is the locking ring 17 and the cylinder 18.

There are six possible dosage setting positions which can be selected by rotating the pointer 8 to the desired position.

In position #1 the puncture pin above drug cell #1 will pierce a cell which is filled with medicament and has no voided area. All the other five puncture pins 4 will pierce the voided regions of cells 2–6 and no medicament will be released from any cell other than drug cell #1.

When the pointer is turned clockwise to position #2 and downward pressure is applied to the upper assembly 2, the puncture pins above drug cells 1 and 2 will pierce the portion of those cells containing medicament 11. All other puncture pins will pierce the voided sections of the other four cells and no medicament will be released from any cells other than numbers 1 and 2.

When the pointer is turned clockwise to position 3, downward pressure will release the medicament in three cells. In position #4 medicament in four cells will be released and in position #5 medicament in five cells will be released.

When the pointer is turned clockwise to position #6 and downward pressure is applied to the upper assembly 2, the puncture pins 4 above all six drug cells will pierce the portions of those cells containing medicament 11. The setting in position #6 will release the maximum medicament dosage of the patch.

Figure 5:
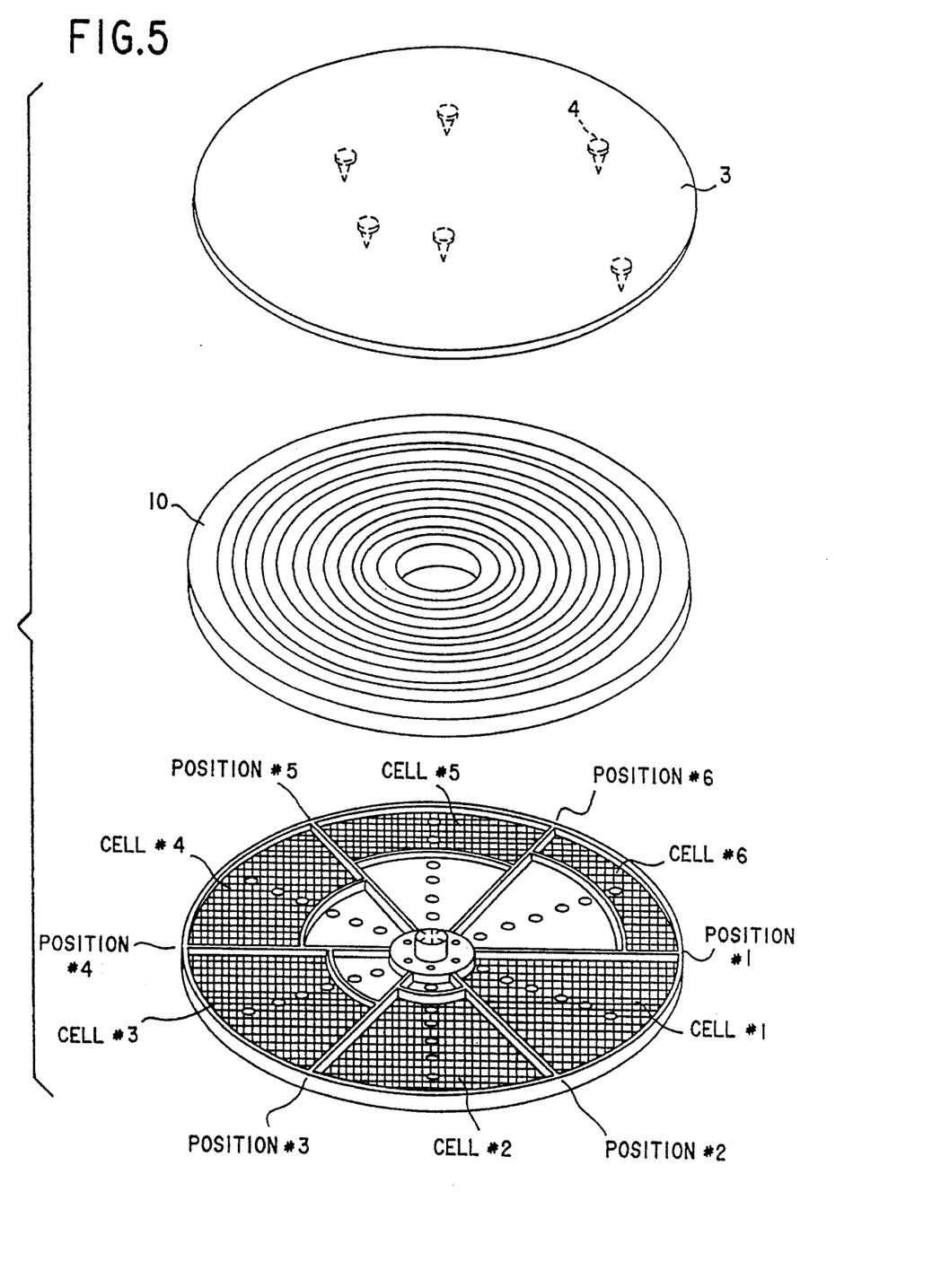
FIG. 5 is a view similar to FIG. 4 showing an upper assembly in the form of a bezel which can be rotated to select the appropriate drug reservoir.

Referring now to FIG. 5 in detail, there is shown a slightly varied embodiment from that of FIG. 4. The entire upper assembly is a bezel which can be rotated to select the required reservoir. This variation circumvents the need for the dial knob 7 and the pointer 8. Naturally, the upper assembly disk 3 is provided with a diameter slightly greater than that of the lower assembly 9, in order to provide a better grip for the hand during the setting of the dosage, i.e. the rotating of the dial 3.

Figure 6:
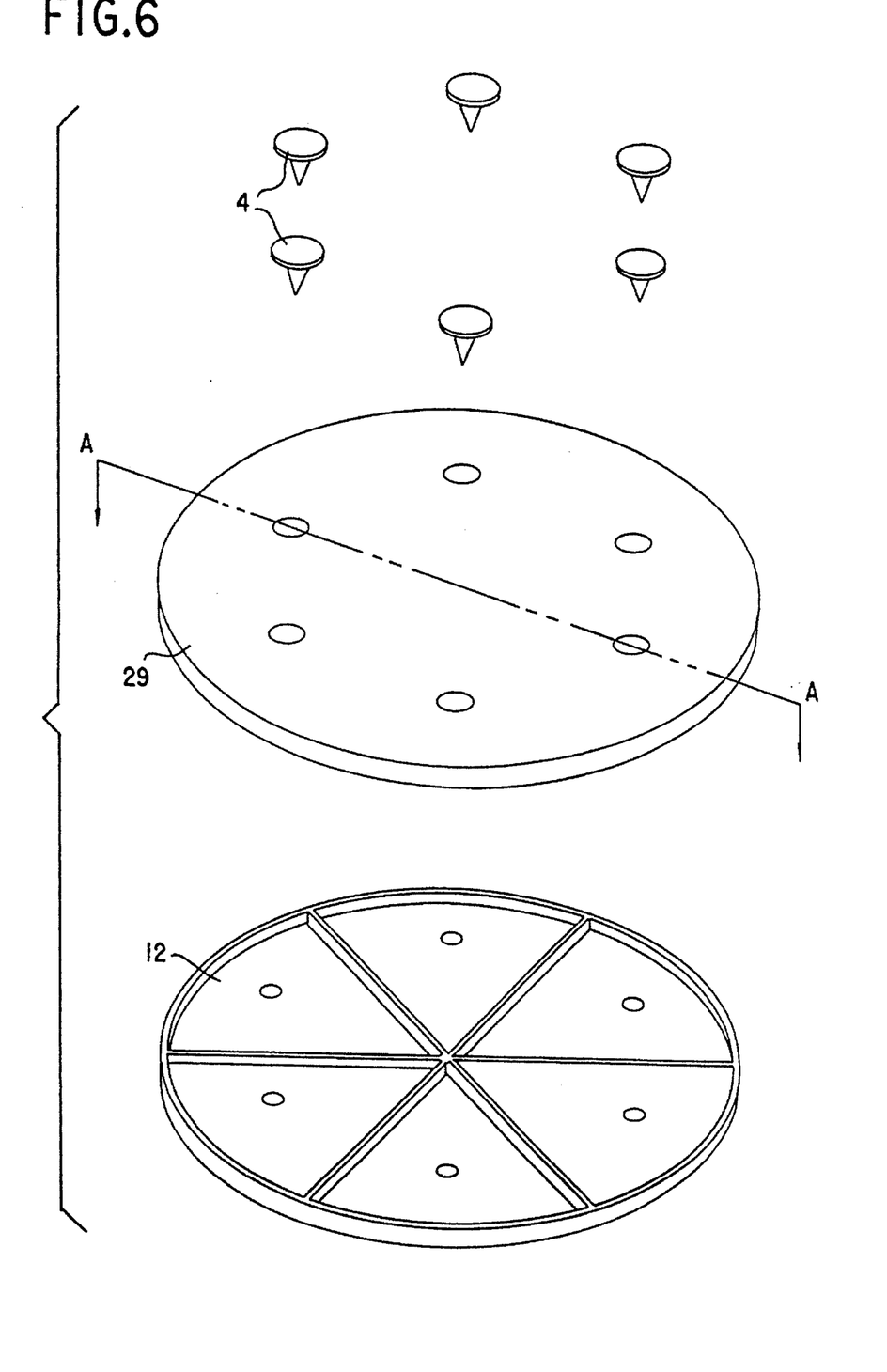
FIG. 6 is a perspective, exploded view of a sequentially delivered unit dose transdermal drug delivery system.
Figure 7:
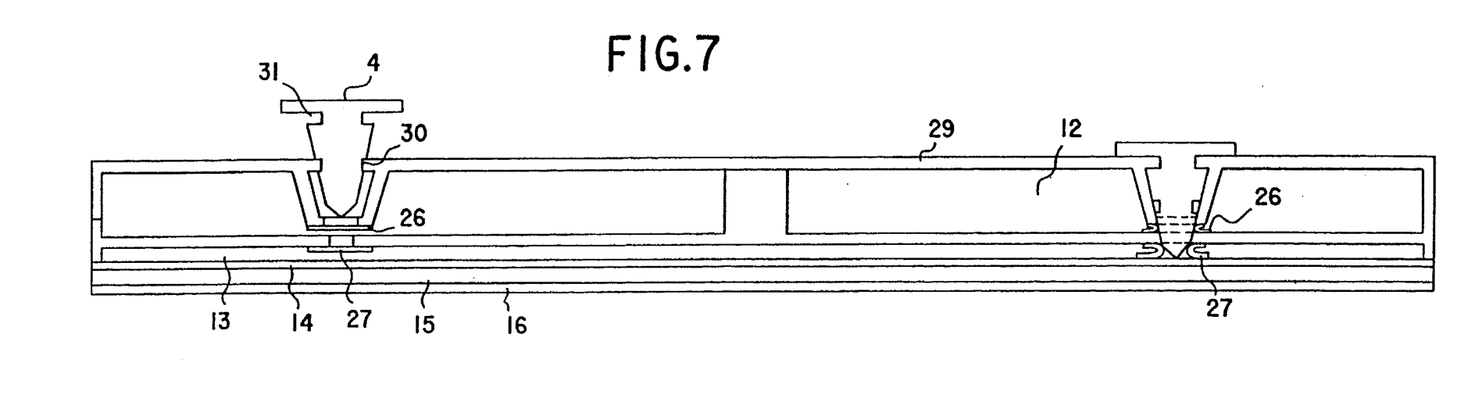
FIG. 7 is a cross-sectional view of the assembly of FIG. 6 as seen along the section plane A—A, the left-hand side of the figure showing a drug reservoir prior to activation and the right-hand side showing a drug reservoir after activation.

Referring now to FIGS. 6 and 7 in detail, there is seen a further embodiment of the invention. The laminate composite shown includes a skin/patch interface membrane 16, transfer gel 15, a protective membrane 14, the capillary distribution space 13 and the sectional drug reservoirs 12. The sectional drug reservoirs each include:

(a) an impervious lower layer impressed therewith into each individual reservoir a window, or plurality of windows, which can be punctured, thereby releasing medicament for contact with the skin of the patient.

(b) an impervious upper layer which is impressed with a plurality of windows which align with the windows in lower layer (a).

The lower assembly 9 includes an alignment plate 29, through which the puncture pins 4 descend, thereby puncturing through upper film 26, and passing through medicament 11 which is contained in the sectional drug reservoir 12, and then continuing to puncture through lower film 27 and into the capillary distribution space 13. The medicament 11 flows past the puncture pins 4 into the capillary distribution space 13, thereby filling the space. Medicament 11 then diffuses through the protective membrane 14, into the transfer gel 15 and through the patch/skin interface membrane 16, after which it is ready for absorption into the skin.

The transfer of the medicament from the drug reservoirs to the capilliary distribution space may be aided by using wicking action, osmotic pressure, a pressurized medicament well or tother means. These aids are known to those skilled in the art to assure the complete and even draining of the desired sectional drug reservoirs.

The alignment plate 29 is provided with a plurality of puncture pins 4. The number of pins 4 corresponds to the number of windows provided in the alignment plate 29 and on the bottom of the reservoirs 12. Each of the pins activates one of the medication reservoirs 12 by the application of downward pressure. Each puncture pin 4 has a preactivation safety lock groove 30 to prevent the accidental release of medicament. When downward pressure is applied to the top of the puncture pin 4, the puncture pin 4 breaks through the preactivation safety lock 30 and descends and is locked into a medicament release position by a post-activation safety lock 31. The pre-activation position of the pin 4 is shown on the left-hand side of FIG. 7 and the post-activation position is shown on the right-hand side.

As a puncture pin locks into the post-activation safety lock 31, an indicating means (visual, olfactory or auditory) will inform the wearer or attendant that the medicament has been activated.

The advantage of this device over existing devices in the industry is that it allows for the sequential, timed delivery of a medicament in a "command-and-demand" fashion. By way of an example, an antibiotic, for example penicillin, is normally prescribed to be taken several times a day, generally per oral. By using the device of the instant specification, the patient can conveniently administer the required dosage via the transdermal route by activation of a reservoir at the prescribed time interval. Another example is seen with medications which require continuous daily dosages over a prescribed course of time, which could now be more effectively administered by the patient. For example, nicotine therapy currently requires daily application of medicament over an extended time frame. Use of the aforementioned transdermal drug delivery system would eliminate the daily changing of nicotine patches, thus assuring better patient compliance.

Figure 8:
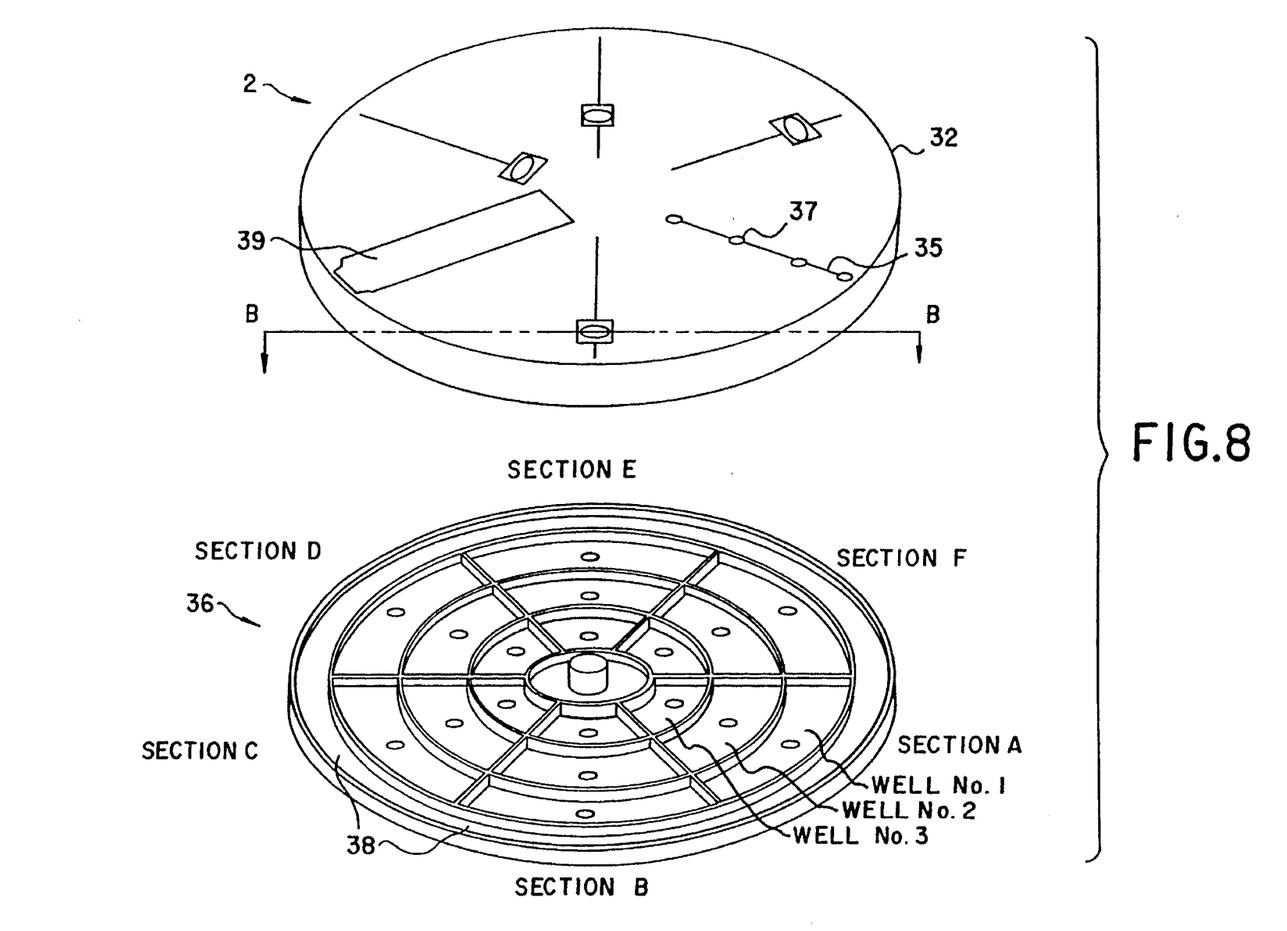
FIG. 8 is a perspective, exploded viw of a sequentially activated, selectable dosage transdermal drug delivery system in a circular configuration.
Figure 9:
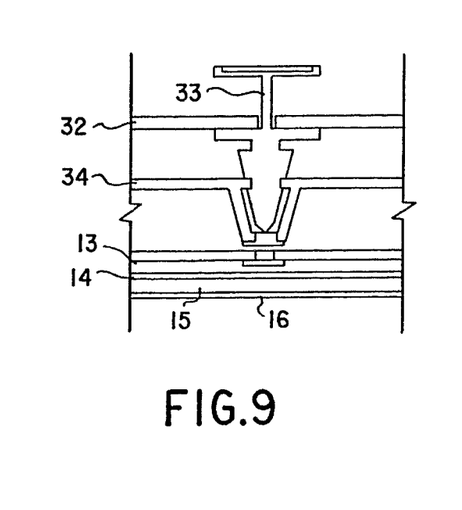
FIG. 9 is a cross-sectional view of the assembly of FIG. 8 as seen along the section plane B—B, prior to activation.
Figure 10:
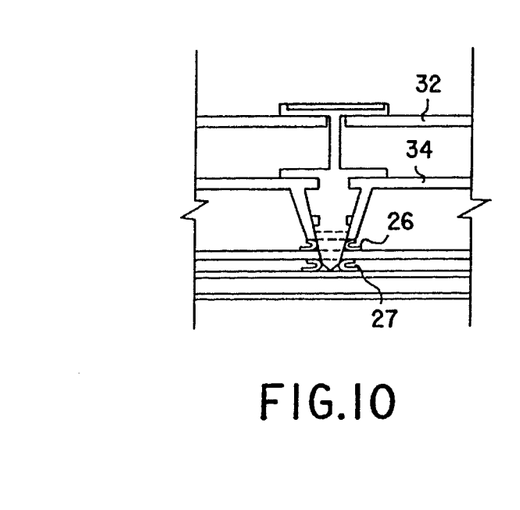
FIG. 10 is a cross-sectional view of the assembly of FIG. 8 as seen along the section plane B—B, after activation.

Referring now to FIGS. 8, 9 and 10 in detail, there is shown a laminate composite including the skin/patch interface membrane 16, the transfer gel 15, the protective membrane 14, the capillary distribution space 13 and a sectional drug reservoir plate 36. The sectional drug reservoir plate includes reservoirs as described above. Again, the windows on the upper assembly align with the windows in the lower layer.

The sectional drug reservoir plate 36 is comprised of individual sections A through F with each section containing three individual medicament wells (1 through 3) and one non-medicament well 38. Each medicament well within a section may contain a different concentration of the medicament within each well.

The upper assembly includes slide carrier plate 32, a plate 29, through which slide puncture pins 33 descend, thereby puncturing through the upper film 26, and passing through the medicament 11 which is contained in the sectional drug reservoir plate 36, and then continuing to puncture through the lower film 27 and into the capillary distribution space 13. The medicament 11 flows past the slide puncture pins 33 into the capillary distribution space 13, thereby filling the space. Thereafter, the medicament 11 diffuses through the protective membrane 14, into the transfer gel 15 and through patch/skin interface membrane 16, until it is ready for absorption into the skin.

Set within the slide carrier plate 32 are slide puncture pins 33 which ride within a slot 35. The slide puncture pins 33 are moved along the slot 35 to select the appropriate drug dosage within each reservoir section.

Each slot 35 and slide puncture pin 33 may be covered by a removeable safety strip 39 which prevents the accidental release of medicament. The safety strip 39 also holds down the slide puncture pins 33 which are initially set in alignment with the non-medicament well 38. The non-medicament well 38 advantageously contains a resilient material which will cause the slide puncture pin 33 to raise up upon removal of the safety strip 39, thereby allowing for the selection of medicament dosage.

Figure 11:
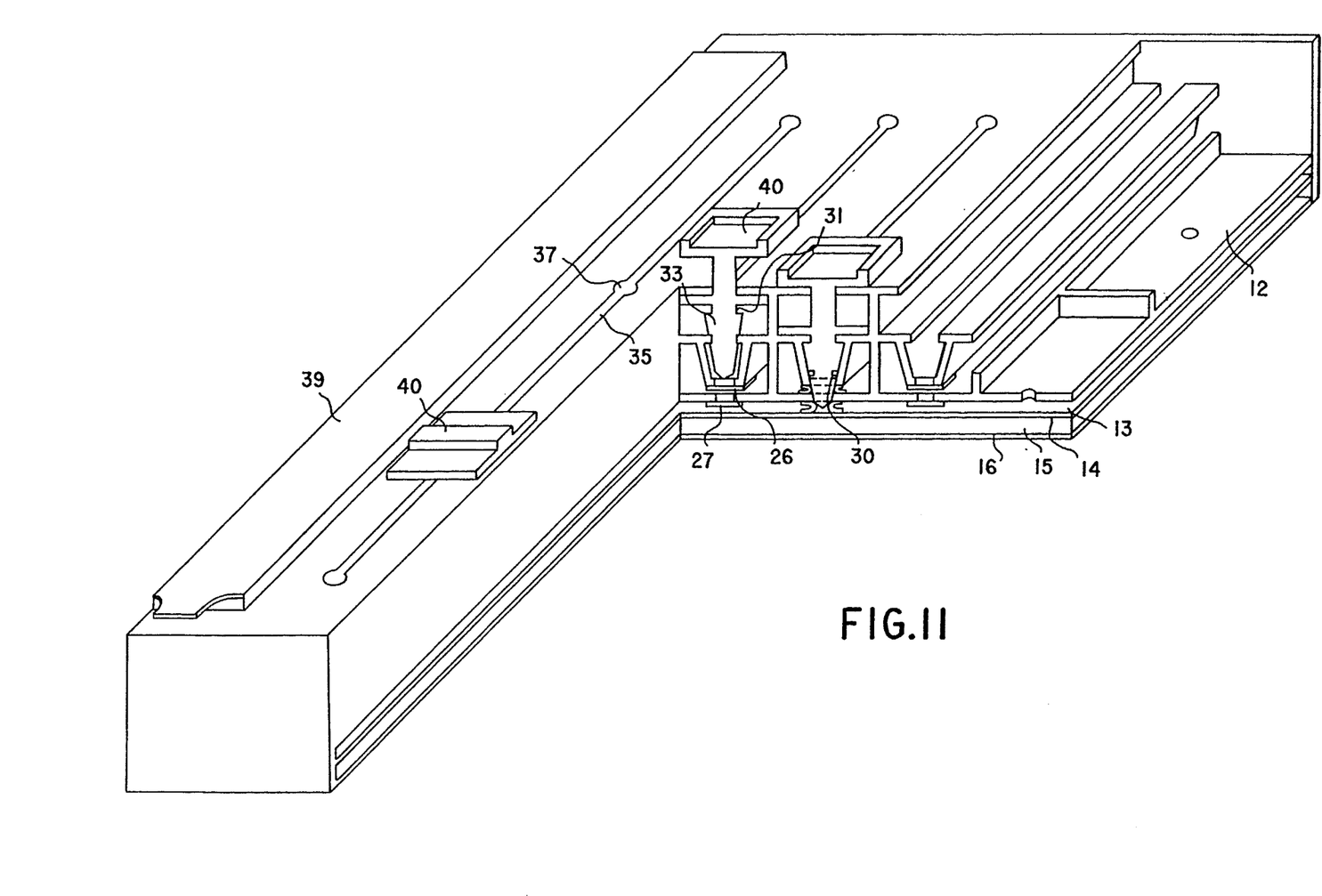
FIG. 11 is a perspective, partly broken-away view of a sequentially activated, selectable dosage transdermal drug delivery system in a rectangular configuration.

The foregoing description, as well as the following information, is applicable to the rectangular embodiment of FIG. 11 as well. The slide puncture pins 35 are moved along the slot 35 to an individual medicament well within a reservoir section by pushing the pin to an alignment notch 37. Each medicament well within the reservoir section has a corresponding alignment notch 37.

Release of the medicament 11 from a medicament well 12 is effected by the action of sliding a puncture pin in slot 35 to the alignment notch 37 which corresponds with the desired medicament and pressing downward on the puncture pin. As the downward pressure is applied to the slide puncture pin, concurrently with the release of the medicament, the slide puncture pin is permanently locked into place by post-activation safety lock 31.

As a puncture pin 35 locks into the post activation safety lock 31, an indicating means (visual, olfactory or auditory) will inform the wearer or attendant that the medicament has been activated.

Each reservoir section may or may not contain similar medicament and each well within the reservoir section may or may not contain uniform variants in concentration of medicament. The advantage of this feature over prior art is that this transdermal drug delivery system allows for the variable dosage selection within a given delivery dispension and concurrently if so desired can administer concomitant medicament as the particular treatment modality may indicate. Additionally, the described invention also allows for the sequential delivery of medicaments over a longer period of time, i.e. several days, by the activation of any reservoir section within that time period.

It is additionally feasible by the removal of post activation safety lock 31 to allow for the multiple delivery of medicament from each reservoir section.

FIG. 11 is a rectangular variation of the embodiment of FIG. 8. The patch of FIG. 11 provides the additional advantage of allowing a more versatile number and size of medicament wells and reservoir sections due to its rectangular configuration. This allows for more variation in its application. For example, a rectangular patch may be more easily secured to certain parts of the anatomy especially in regard to smaller or younger users.

The puncture pins 33 are individually actuable by the application of downward pressure. Each puncture pin has a preactivation safety lock groove 30 to prevent the accidental release of medicament. When downward pressure is applied to the top of puncture pin 4, the puncture pin breaks through preactivation safety lock 30 and descends and is locked into the medicament release position via post activation safety lock 31.

Figure 12A:
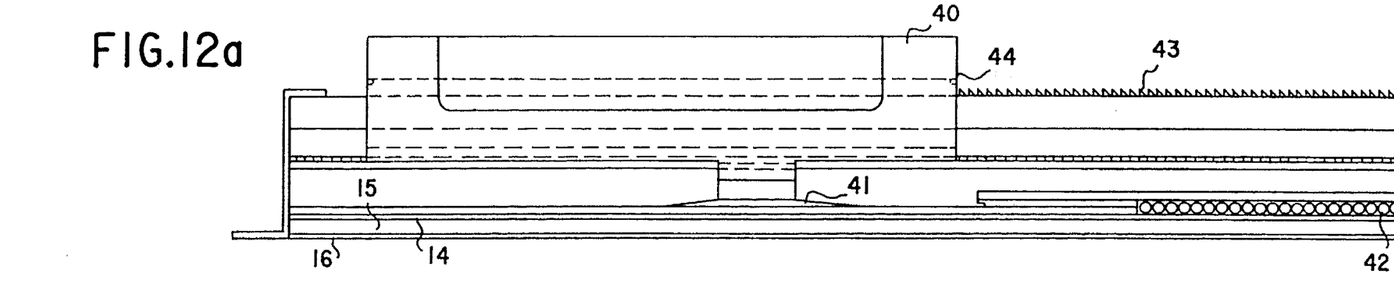
FIGS. 12a, 12b and 12c are enlarged, partial, cross-sectional views of a transdermal drug delivery system with micro-encapsulated medicament.
Figure 12B:
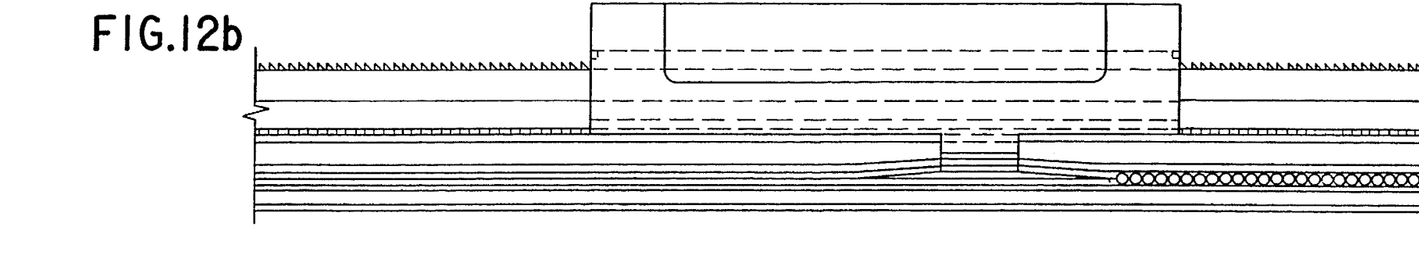
Figure 12C:
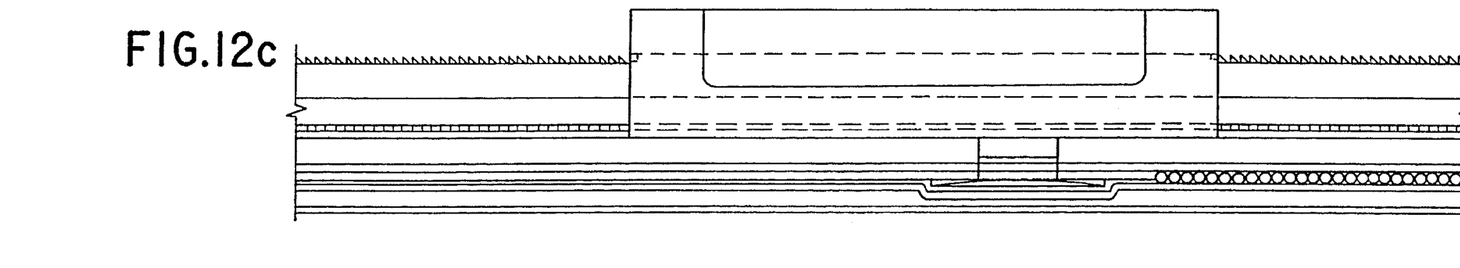
Figure 13A:
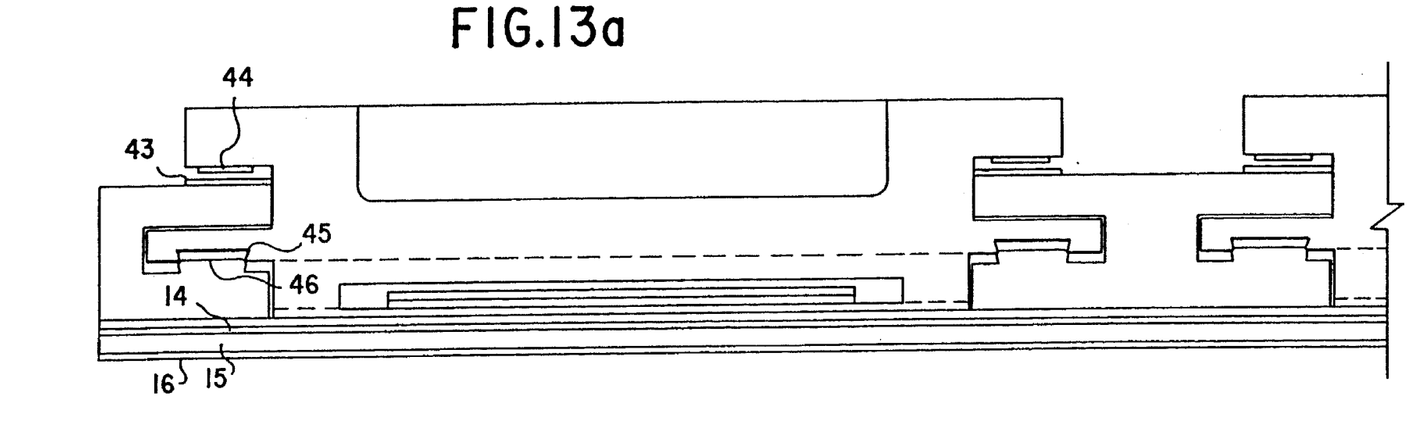
FIG. 13a is an cross-sectional view of the embodiment of FIG. 12 as seen perpendicular to FIGS. 12a–12c with the selectable dosage tab or slide tab in a sliding position.
Figure 13B:
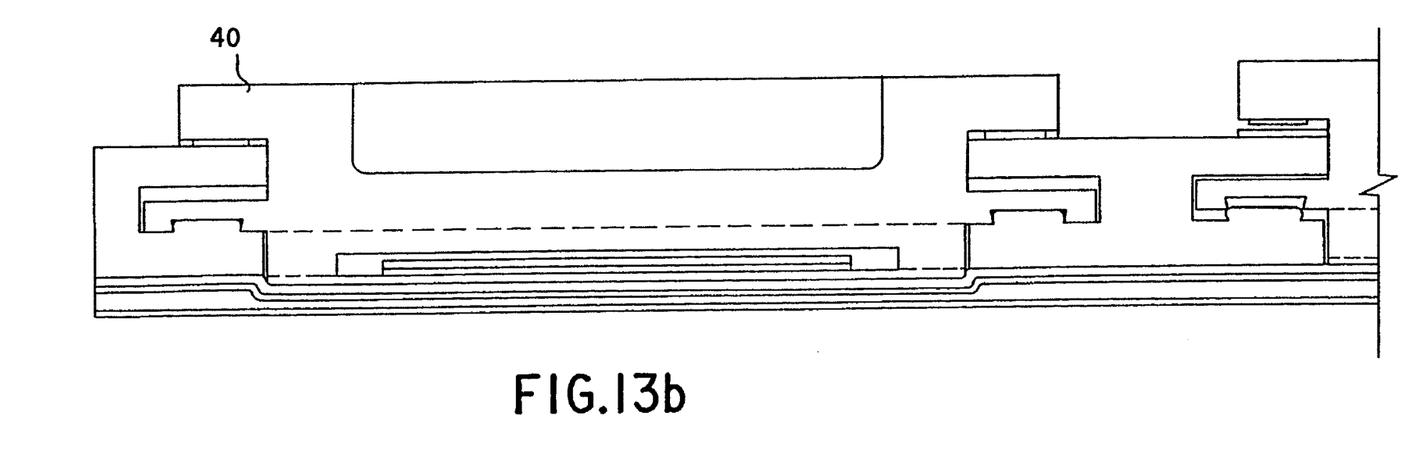
FIG. 13b is a view similar to FIG. 13a, showing the tab in a locked position.

Referring now to FIGS. 12 and 13 in detail, which show a further embodiment of the invention, the slide tabs 40 are not connected to internal puncture pins, as shown in FIG. 11, but instead to an activation mechanism for micro-encapsulated medicament. General information on micro-encapsulation and the tear-and-release action associated therewith may be found in copending applications Ser. No. 865,309, filed Apr. 8, 1992, and Ser. No. 07/927,837, filed Aug. 10, 1992, of which the instant application is a continuation-in-part. The disclosures of those applications are herewith incorporated by reference.

A wedge-shaped attachment 41 on the slide tab 40 slides along the medicament layer 42 and thus tears and releases a given amount of micro-encapsulated medicament upon contact. With reference to FIG. 12c, for instance, the medicament capsules on the right are not broken yet, the region under the wedge-shaped attachment 41 is passive in terms of medicament transfer, and the region to the left of the wedge-shaped attachment 41 now transfers medicament to the patient's skin. The layers 14, 15 and 16 are permeable, and thus allow the medication to proceed from the medicament layer to the patient's skin.

A ratchet-type surface 43 provides a certain resistance against sliding by the slide tab 40. After the slide tab 40 has been moved a given distance, i.e. it has raptured a given number of micro-capsules and has released a given amount of medicament, the slide tab 40 is pushed downward.

The ratchets 43 now engage in corresponding notches 44 provided on the slide tab 40. Due to the pitch of the ratchet surface 43, the slide tab 40 may still be moved towards the left in FIG. 12, but not towards the right, which would cause more medicament to be released. Furthermore, a dove-tail locking mechanism 45, 46 is provided for the slide tab 40. When the slide tab 40 is pressed downward, the tail 46 hooks into the corresponding cutout 45 and thus holds the tab 40 in its lower position. The slide tab 40 on the left-hand side of FIG. 13 is shown in the locked position, while the adjacent slide tab 40 partially shown on the right-hand side is in the sliding, i.e. upper position.

All embodiments of the invention may also, if needed, include a means for transferring medicament from the drug reservoirs by the use of wicking action, osmotic pressure, pressurized medicament well or other means known to those skilled in the art to assure the complete and even draining of the drug reservoir.

We claim:

1. A transdermal drug delivery system, comprising a laminate composite of:
   (a) a first permeable membrane to be placed in contact with a patient's skin;
   (b) a transfer gel layer disposed on said first permeable membrane;
   (c) a second permeable membrane disposed on said transfer gel layer;
   (d) a reservoir layer disposed above said second permeable membrane, said reservoir layer being formed of medicament micro-encapsulated in a multiplicity of frangible microspheres; and
   (e) activation means for activating said microspheres and releasing a given amount of medicament from said microspheres in said reservoir layer for contact with the patient's skin, said activation means including a slide tab with a wedge mechanism for rupturing said microspheres.

2. The drug delivery system according to claim 1, wherein said reservoir layer is formed of strips of micro-encapsulated medicament, said strips being separated from one another, and wherein said slide tab with the wedge mechanism variably activates a given amount of microencapsulated medicament of a respective one of said strips.

\* \* \* \* \*